United States Patent
Takauji et al.

(10) Patent No.: US 11,319,484 B2
(45) Date of Patent: May 3, 2022

(54) ELECTROCHROMIC ELEMENT AND METHOD FOR MANUFACTURING ELECTROCHROMIC ELEMENT

(71) Applicant: Ricoh Company, Ltd., Tokyo (JP)

(72) Inventors: Keigo Takauji, Kanagawa (JP); Satoshi Yamamoto, Kanagawa (JP); Fuminari Kaneko, Kanagawa (JP); Kazuaki Tsuji, Kanagawa (JP); Naoki Ura, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 295 days.

(21) Appl. No.: 16/393,416

(22) Filed: Apr. 24, 2019

(65) Prior Publication Data

US 2019/0324338 A1    Oct. 24, 2019

(30) Foreign Application Priority Data

Apr. 24, 2018 (JP) .............................. JP2018-082695
Apr. 19, 2019 (JP) .............................. JP2019-079767

(51) Int. Cl.
*G02F 1/15* (2019.01)
*G02F 1/1516* (2019.01)
(Continued)

(52) U.S. Cl.
CPC .............. *C09K 9/02* (2013.01); *C07C 203/08* (2013.01); *G02F 1/1503* (2019.01); *G02F 1/15165* (2019.01); *C09K 2211/1022* (2013.01)

(58) Field of Classification Search
CPC .... G02F 1/153; G02F 1/1503; G02F 1/15165; G02F 2001/1515; G02F 1/1516; C09K 9/02; C09K 2211/1044

See application file for complete search history.

(56) References Cited

U.S. PATENT DOCUMENTS

| | | |
|---|---|---|
| 2015/0274761 A1 | 10/2015 | Sagisaka et al. |
| 2015/0331295 A1 | 11/2015 | Takahashi et al. |

(Continued)

FOREIGN PATENT DOCUMENTS

| | | |
|---|---|---|
| JP | 1-231028 | 9/1989 |
| JP | 2016-038572 | 3/2016 |

*Primary Examiner* — Bijan Ahvazi
(74) *Attorney, Agent, or Firm* — Xsensus LLP

(57) ABSTRACT

An electrochromic element is provided including: a first substrate; a first electrode overlying the first substrate; a second substrate disposed at a distance from the first electrode; a second electrode overlying the second substrate; a first electrochemical reaction layer in contact with the first electrode; a second electrochemical reaction layer in contact with the second electrode; and an electrolyte layer between the first electrode and the second electrode. One of the first electrochemical reaction layer and the second electrochemical reaction layer is in a reversibly oxidizable state and the other is in a reversibly reducible state, at least one of the first electrochemical reaction layer and the second electrochemical reaction layer is an electrochromic layer, and $E1 \geq -0.8$ V (vs. $FC/FC^+$) and $E2 \geq -0.8$ V (vs. $FC/FC^+$) are satisfied, where E1 and E2 represent oxidation-reduction potentials of the first electrochemical reaction layer and the second electrochemical reaction layer, respectively.

8 Claims, 1 Drawing Sheet

(51) Int. Cl.
*C09K 9/02* (2006.01)
*G02F 1/1503* (2019.01)
*C07C 203/08* (2006.01)

(56) References Cited

U.S. PATENT DOCUMENTS

| | | |
|---|---|---|
| 2016/0005375 A1 | 1/2016 | Naijo et al. |
| 2016/0108072 A1 | 4/2016 | Inoue et al. |
| 2016/0209721 A1 | 7/2016 | Matsumoto et al. |
| 2017/0010514 A1 | 1/2017 | Yashiro et al. |
| 2017/0131609 A1 | 5/2017 | Okada et al. |
| 2017/0168366 A1 | 6/2017 | Shinoda et al. |
| 2017/0226413 A1 | 8/2017 | Goto et al. |
| 2017/0235203 A1* | 8/2017 | Yamamoto ............ G02F 1/155 359/268 |
| 2017/0329197 A1 | 11/2017 | Yashiro et al. |
| 2017/0329198 A1 | 11/2017 | Matsuoka et al. |
| 2017/0329199 A1 | 11/2017 | Yashiro et al. |
| 2017/0336691 A1 | 11/2017 | Yamamoto et al. |
| 2018/0044581 A1 | 2/2018 | Sagisaka et al. |
| 2018/0113366 A1 | 4/2018 | Kaneko et al. |
| 2018/0173070 A1 | 6/2018 | Yamamoto et al. |
| 2018/0208834 A1 | 7/2018 | Goto et al. |
| 2018/0314125 A1 | 11/2018 | Goto et al. |
| 2019/0031694 A1 | 1/2019 | Sagisaka et al. |

* cited by examiner

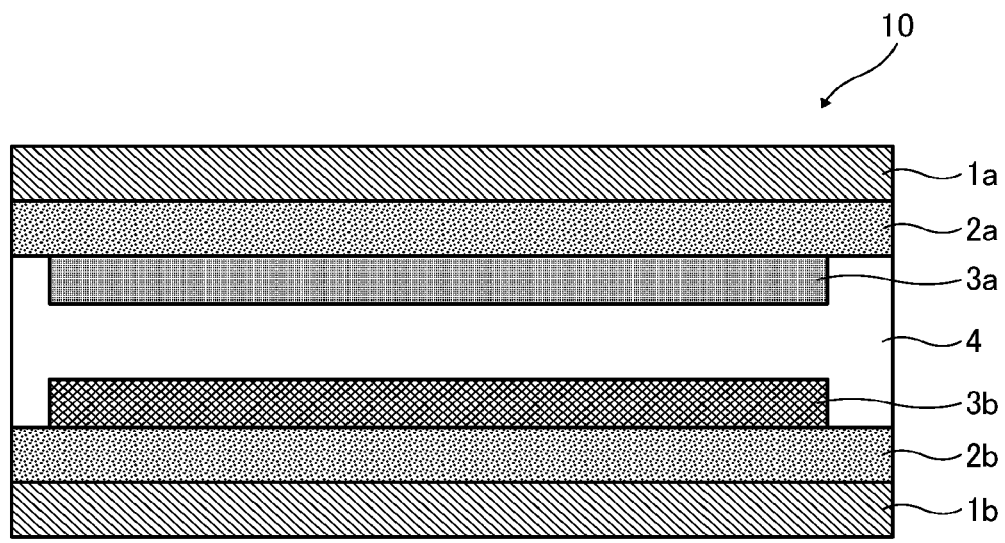

ELECTROCHROMIC ELEMENT AND METHOD FOR MANUFACTURING ELECTROCHROMIC ELEMENT

CROSS-REFERENCE TO RELATED APPLICATIONS

This patent application is based on and claims priority pursuant to 35 U.S.C. § 119(a) to Japanese Patent Application Nos. 2018-082695 and 2019-079767, filed on Apr. 24, 2018 and Apr. 19, 2019, respectively, in the Japan Patent Office, the entire disclosure of which is hereby incorporated by reference herein.

BACKGROUND

Technical Field

The present disclosure relates to an electrochromic element and a method for manufacturing an electrochromic element.

Description of the Related Art

An electrochromic element used for light control applications and signage applications is required to have high memory performance to maintain a colored state even when applied with a low voltage or no voltage. Assuming outdoor use, it is desired that the electrochromic element can be stably driven in the atmosphere for an extended period of time. However, it is particularly difficult for an electrochromic element using an organic material to secure memory performance and stability under the atmosphere.

As an electrochromic organic compound, a viologen compound is known. The viologen compound is transparent in a neutral state and exhibits an electrochromic phenomenon in a reduced state to develop color. However, the viologen compound colored in the reduced state may be immediately decolored by oxidation action when exposed to oxygen in the atmosphere. It is difficult to stably operate the element unless the element is strictly sealed.

In view of this situation, there has been an attempt to eliminate instability of viologen compounds in color development by using an organic solvent in an electrolyte layer and providing a polymer gel on the surface of a display electrode.

In addition, a triarylamine compound has been proposed as an electrochromic material which is transparent in a neutral state and colored in an oxidized state. It has been reported that this triarylamine compound colored in the oxidized state is stable irrespective of oxygen in the air.

SUMMARY

In accordance with some embodiments of the present invention, an electrochromic element is provided. The electrochromic element includes: a first substrate; a first electrode overlying the first substrate; a second substrate disposed at a distance from the first electrode; a second electrode overlying the second substrate; a first electrochemical reaction layer in contact with the first electrode; a second electrochemical reaction layer in contact with the second electrode; and an electrolyte layer between the first electrode and the second electrode. One of the first electrochemical reaction layer and the second electrochemical reaction layer is in a reversibly oxidizable state and the other is in a reversibly reducible state, at least one of the first electrochemical reaction layer and the second electrochemical reaction layer is an electrochromic layer, and the following formulae are satisfied:

$$E1 \geq -0.8 \text{ V (vs. FC/FC}^+\text{)}$$

$$E2 \geq -0.8 \text{ V (vs. FC/FC}^+\text{)}$$

where $E1$ represents an oxidation-reduction potential of the first electrochemical reaction layer and $E2$ represents an oxidation-reduction potential of the second electrochemical reaction layer.

In accordance with some embodiments of the present invention, a method for manufacturing an electrochromic element is provided. The method includes the processes of: forming a first electrode and a first electrochemical reaction layer on a first substrate; forming a second electrode and a second electrochemical reaction layer on a second substrate; bonding the first substrate and the second substrate via an electrolyte layer; and oxidizing at least one of the first electrochemical reaction layer and the second electrochemical reaction layer.

BRIEF DESCRIPTION OF THE DRAWING

A more complete appreciation of the disclosure and many of the attendant advantages thereof will be readily obtained as the same becomes better understood by reference to the following detailed description when considered in connection with the accompanying drawing, which is intended to depict example embodiments of the present invention and should not be interpreted to limit the scope thereof. The accompanying drawing is not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Embodiments of the present invention are described in detail below with reference to accompanying drawings. In describing embodiments illustrated in the drawings, specific terminology is employed for the sake of clarity. However, the disclosure of this patent specification is not intended to be limited to the specific terminology so selected, and it is to be understood that each specific element includes all technical equivalents that have a similar function, operate in a similar manner, and achieve a similar result.

For the sake of simplicity, the same reference number will be given to identical constituent elements such as parts and materials having the same functions and redundant descriptions thereof omitted unless otherwise stated.

Within the context of the present disclosure, if a first layer is stated to be "overlaid" on, or "overlying" a second layer, the first layer may be in direct contact with a portion or all of the second layer, or there may be one or more intervening layers between the first and second layer, with the second layer being closer to the substrate than the first layer.

According to an embodiment of the present invention, an electrochromic element exhibiting excellent color retention property and drive stability even under the atmosphere without requiring strict sealing is provided.

Electrochromic Element

The electrochromic element according to an embodiment of the present invention includes a first substrate, a first electrode overlying the first substrate, a second substrate disposed at a distance from the first electrode, a second electrode overlying the second substrate, a first electrochemical reaction layer in contact with the first electrode, a second electrochemical reaction layer in contact with the second electrode, and an electrolyte layer between the first electrode and the second electrode, where one of the first electrochemical reaction layer and the second electrochemical reaction layer is in a reversibly oxidizable state and the other is in a reversibly reducible state, at least one of the first electrochemical reaction layer and the second electrochemical reaction layer is an electrochromic layer, and the following formulae are satisfied: $E1 \geq -0.8$ V (vs. $FC/FC^-$) and $E2 \geq -0.8$ V (vs. $FC/FC^-$), where E1 represents an oxidation-reduction potential of the first electrochemical reaction layer and E2 represents an oxidation-reduction potential of the second electrochemical reaction layer. The electrochromic element further optionally includes other layers as necessary. Here, FC refers to ferrocene and $FC^+$ refers to ferrocenium ion.

The electrochromic element according to an embodiment of the present invention is achieved based on a finding that a conventional method of improving the degree of sealing is not expected to deliver significant improvement because durability of a material itself against oxygen is not necessarily improved.

In addition, a counter electrode material to be paired with the conventional triarylamine compound to undergo the reverse reaction of the reaction of the triarylamine compound has not been proposed. As general counter electrode materials, metal oxides such as titanium oxide exhibiting semiconducting properties and metal oxides carrying a reducing material on the surface have been researched. However, since metal oxides themselves are photoactive, drive stability under light irradiation may not be sufficiently secured. Thus, the electrochromic element according to an embodiment of the present invention is also based on another finding that it is difficult to produce an electrochromic element exhibiting high stability in the atmosphere depending on the reducing material to be used for the same reason as the viologen compound.

According to an embodiment of the present invention, one of the first electrochemical reaction layer and the second electrochemical reaction layer is in a reversibly oxidizable state and the other is in a reversibly reducible state, at least one of the first electrochemical reaction layer and the second electrochemical reaction layer is an electrochromic layer, and the following formulae are satisfied: $E1 \geq -0.8$ V (vs. $FC/FC^+$) and $E2 \geq -0.8$ V (vs. $FC/FC^+$), where E1 represents an oxidation-reduction potential of the first electrochemical reaction layer and E2 represents an oxidation-reduction potential of the second electrochemical reaction layer.

When the oxidation-reduction potentials E1 and E2 of the respective first and second electrochemical reaction layers are $-0.8$ V (vs. $FC/FC^+$) or higher, the first and second electrochemical reaction layers are less susceptible to oxidation action by oxygen even under the atmosphere and can be stably present in the atmosphere.

For example, it is known that the oxidation-reduction potential of a viologen compound at one-electron reduction from a dication state is about $-0.9$ V (vs. $FC/FC'$). Such a viologen compound is susceptible to oxidation action by oxygen present in the atmosphere, and as a result, the viologen compound in a colored state is instantaneously subjected to one-electron reduction in the atmosphere, returned to the dication state, and decolored.

A compound having a triarylamine structure, the oxidation-reduction potential of which between the neutral state and the radical cation state is around 0.3 V, can be stably present both in colored and decolored states even under the atmosphere without being instantaneously oxidized and put in the radical cation state.

In the case of a compound taking a neutral state and a radical cation state, such as a compound having a triarylamine structure, it is preferable that one of the first and second electrochemical reaction layers has an oxidation-reduction potential of 0.0 V (vs. $FC/FC^+$) or higher and lower than 0.2 V (vs. $FC/FC^+$) and the other has an oxidation-reduction potential of from 0.2 to 0.5 V (vs. $FC/FC^+$).

The electrochemical reaction layer having an oxidation-reduction potential of 0.0 V (vs. $FC/FC^+$) or higher and lower than 0.2 V (vs. $FC/FC^+$) is very stable in a one-electron-oxidized radical cation state and can be kept in the radical cation state for an extended period of time. When the oxidation-reduction potential is lower than this, the electrochemical reaction layer may be gradually oxidized by oxygen with time although the degree of oxidation is small, and reduction of stability in the neutral state may be concerned.

The electrochemical reaction layer having an oxidation-reduction potential of from 0.2 to 0.5 V (vs. $FC/FC^+$) is relatively stable in both the neutral state and the radical cation state. Therefore, it is easy to electrochemically change both states. When the oxidation-reduction potential is higher than this, the electrochemical reaction layer is highly stable in the neutral state, and it is difficult to achieve a stable radical cation state.

Accordingly, when the two electrochemical reaction layers have different oxidation-reduction potentials, at least one of the first electrochemical reaction layer and the second electrochemical reaction layer can be constantly kept in the radical cation state.

To constantly keep at least one of the first electrochemical reaction layer and the second electrochemical reaction layer in the radical cation state, at least one of the first electrochemical reaction layer and the second electrochemical reaction layer is subjected to an oxidation treatment. The oxidation treatment will be described in detail later in explaining the method of manufacturing electrochromic element.

Preferably, the oxidation-reduction potential E1 of the first electrochemical reaction layer and the oxidation-reduction potential E2 of the second electrochemical reaction layer satisfy the following formula: $|E1-E2|<0.9$ V. When the difference between the two oxidation-reduction potentials is less than 0.9 V, the driving voltage is also small, and improvement in memory performance (color retention time) can be expected due to a small energy difference between the colored and decolored states.

Preferably, the first electrochemical reaction layer and the second electrochemical reaction layer each comprise an electrochemically active material capable of being in a radical cation state, at least one of the first electrochemical reaction layer and the second electrochemical reaction layer is constantly in the radical cation state, and the following formulae are satisfied: $E1' \geq -0.8$ V (vs. $FC/FC^+$) and $E2' \geq -0.8$ V (vs. $FC/FC^+$), where E1' represents an oxidation-reduction potential between a neutral state and the radical cation state of the first electrochemical reaction layer and E2' represents an oxidation-reduction potential between a neutral state and the radical cation state of the second electrochemical reaction layer, for wide selection of the material of an electrolytic solution that does not contribute to reactions.

The oxidation-reduction potential E1' between the neutral state and the radical cation state of the first electrochemical reaction layer and the oxidation-reduction potential E2' between the neutral state and the radical cation state of the second electrochemical reaction layer may be measured by cyclic voltammetry.

The electrochromic element according to an embodiment of the present invention includes a first substrate, a first electrode overlying the first substrate, a second substrate disposed at a distance from the first electrode, a second electrode overlying the second substrate, a first electrochemical reaction layer in contact with the first electrode, a second electrochemical reaction layer in contact with the second electrode, and an electrolyte layer between the first electrode and the second electrode, and further optionally includes other layers as necessary.

First Substrate and Second Substrate

The first substrate has a function of supporting the first electrode and the first electrochemical reaction layer.

The second substrate has a function of supporting the second electrode and the second electrochemical reaction layer.

As the substrate, any known organic material or inorganic material can be used as long as it is a transparent material capable of supporting these layers.

Specific examples of the substrate include, but are not limited to, a glass substrate made of non-alkali glass, borosilicate glass, float glass, or soda-lime glass.

In addition, a resin substrate made of polycarbonate resin, acrylic resin, polyethylene, polyvinyl chloride, polyester, epoxy resin, melamine resin, phenol resin, polyurethane resin, or polyimide resin may also be used as the substrate. The substrate may have a surface coating such as a transparent insulating layer and an antireflection layer, for improving vapor barrier property, gas barrier property, and visibility.

The shape of the substrate is not particularly limited and may be rectangular or circular. Moreover, the substrate may be in a spherical structure like a lens.

First Electrode and Second Electrode

The first electrode and the second electrode are not particularly limited as long as they are conductive materials and one or both of them is/are transparent. The contrast of coloring can be increased by such a configuration.

Examples of transparent conductive materials include, but are not limited to, inorganic materials such as tin-doped indium oxide ("ITO"), fluorine-doped tin oxide ("FTO"), and antimony-doped tin oxide ("ATO"). In particular, an inorganic material comprising one of indium oxide ("In oxide"), tin oxide ("Sn oxide"), and zinc oxide ("Zn oxide"), formed by vacuum film formation, is preferred.

In oxide, Sn oxide, and Zn oxide can be easily formed into a film by sputtering, have good transparency, and exhibit electric conductivity. In particular, InSnO, GaZnO, SnO, $In_2O_3$, and ZnO are preferred.

Alternatively, an electrode having improved conductivity while maintaining transparency may be used, formed of a fine network structure of transparent carbon nanotube or other highly-conductive non-transmissive materials such as Au, Ag, Pt, and Cu.

The thicknesses of the first electrode and the second electrode are so adjusted that these electrodes have proper electrical resistance values required for causing a redox reaction in the electrochromic layer. In a case in which the first electrode and the second electrode each comprise ITO, the thicknesses of each of the first electrode and the second electrode is preferably from 50 to 500 nm.

The first electrode and the second electrode may be formed by, for example, vacuum vapor deposition, sputtering, or ion plating.

In addition, the first electrode and the second electrode can also be formed by any coating method, such as spin coating, casting, micro gravure coating, gravure coating, bar coating, roll coating, wire bar coating, dip coating, slit coating, capillary coating, spray coating, nozzle coating, or various printing methods, such as gravure printing, screen printing, flexo printing, offset printing, reverse printing, and inkjet printing.

When transparency is unnecessary, a plate of a metal such as titanium and zinc can also be used.

The optical transmittance of the transparent electrode is not particularly limited and can be appropriately selected according to the purpose, but is preferably 60% or more and less than 100%, and more preferably 90% or more and less than 100%. When the optical transmittance is less than 60%, displayed images become dark and display performance such as brightness and vividness deteriorates. The film thickness of the transparent electrode is not particularly limited, but is preferably from 10 to 300 nm in the case of an ITO electrode.

First Electrochemical Reaction Layer and Second Electrochemical Reaction Layer

According to an embodiment of the present invention, the first electrochemical reaction layer and the second electrochemical reaction layer each comprise an electrochemically active material, one of the first electrochemical reaction layer and the second electrochemical reaction layer is in a reversibly oxidizable state and the other is in a reversibly reducible state, and at least one of the first electrochemical reaction layer and the second electrochemical reaction layer is an electrochromic layer.

Here, an electrochemical reaction layer having a reversibly oxidizable state specifically refers to a layer containing a compound having the following characteristics. That is, a compound having a reversibly oxidizable state. This compound is capable of donating one or more electrons, becoming electron-accepting after donating electrons, and returning to the initial compound after accepting electrons.

Here, an electrochemical reaction layer having a reversibly reducible state specifically refers to a layer containing a compound having the following characteristics. That is, a compound having a reversibly reducible state. This compound is capable of accepting one or more electrons, becoming electron-donating after accepting electrons, and returning to the initial compound after donating electrons.

Preferably, at least one of the first electrochemical reaction layer and the second electrochemical reaction layer is an electrochromic layer that develops color when in a radical cation state, and only one of the first electrochemical reaction layer and the second electrochemical reaction layer is the electrochromic layer, for improving display quality in applications for displaying vivid color such as signage applications.

When the electrochemical reaction layers are in the above-described configuration, a counter electrochemical reaction layer may be provided that undergoes an electrochemical reaction without a large color change. The counter electrochemical reaction layer carries out the reverse reaction of the electrochromic layer to stabilize the electrochemical reactions with an expectation of reducing the potential difference required for the electrochromic reaction. In the case where the electrochromic layer is of the oxidative coloring type, it is preferable that the counter electrochemical reaction layer comprise a material of the reductive type.

The material used for the electrochemical reaction layer may be either an inorganic compound and an organic compound. Since the electrochemical reaction layer can be regarded as an electrochromic material in which a change in the light absorption band in the visible light range accompanying a redox reaction is small (almost no color change), the same material for the electrochromic layer can be used therefor.

The electrochemical reaction layer can be formed by vacuum vapor deposition, sputtering, or ion plating. In addition, spin coating, casting, micro gravure coating, gravure coating, bar coating, roll coating, wire bar coating, dip coating, slit coating, capillary coating, spray coating, nozzle coating, and various printing methods such as gravure printing, screen printing, flexographic printing, offset printing, reverse printing, and inkjet printing may also be used.

The electrochromic layer contains an electrochromic material, and the electrochromic material may be either an inorganic electrochromic compound or an organic electrochromic compound. In addition, a conductive polymer known to exhibit electrochromism can also be used as the electrochromic material.

Examples of the inorganic electrochromic compound include, but are not limited to, tungsten oxide, molybdenum oxide, iridium oxide, and titanium oxide. Examples of the organic electrochromic compound include, but are not limited to, viologen, rare-earth phthalocyanine, and styryl.

Examples of the conductive polymer include, but are not limited to, polypyrrol, polythiophene, polyaniline, and derivatives thereof.

Specific examples thereof include, but are not limited to, polymer-based and dye-based electrochromic compounds including: low-molecular-weight organic electrochromic compounds such as azobenzene compounds, anthraquinone compounds, diarylethene compounds, dihydroprene compounds, dipyridine compounds, styryl compounds, styrylspiropyran compounds, spirooxazine compounds, spirothiopyran compounds, thioindigo compounds, tetrathiafulvalene compounds, terephthalic acid compounds, triphenylmethane compounds, triarylamine compounds, naphthopyran compounds, viologen compounds, pyrazoline compounds, phenazine compounds, phenylenediamine compounds, phenoxazine compounds, phenothiazine compounds, phthalocyanine compounds, fluoran compounds, fulgide compounds, benzopyran compounds, and metallocene compounds; and conductive polymer compounds such as polyaniline and polythiophene.

Among these, a compound having a triarylamine backbone is preferable, and a triarylamine-containing radical polymerizable compound having both a triarylamine backbone represented by the following general formula 1 and a radical polymerizable functional group is particularly preferable.

When the electrochromic layer contains a compound having a triarylamine backbone represented by the following general formula 1, repetitive drive (redox reaction) performance and light durability are advantageously excellent. In addition, the electrochromic layer is transparent in a decolored state and develops high-density color upon oxidation reaction.

$$A_n\text{-}B_m \qquad \text{[General Formula 1]}$$

In the general formula 1, when n is 2, m is 0; and when n is 1, m is 0 or 1. A has a structure represented by the following general formula 2 and bound to B at any of positions $R_1$ to $R_{15}$. B has a structure represented by the following general formula 3 and bound to A at any of positions of $R_{16}$ to $R_{21}$.

[General Formula 2]

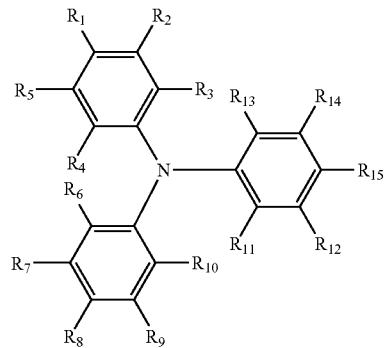

[General Formula 3]

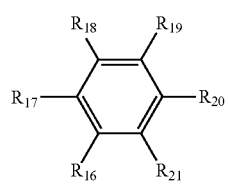

In the general formulae 2 and 3, $R_1$ to $R_{21}$ each independently represent monovalent organic groups, and at least one of the monovalent organic groups is a radical polymerizable functional group.

Monovalent Organic Group

Specific examples of the monovalent organic group in the general formulae 2 and 3 include, but are not limited to, a hydrogen atom, a halogen atom, hydroxyl group, nitro group, cyano group, carboxyl group, a substituted or unsubstituted alkoxycarbonyl group, a substituted or unsubstituted aryloxycarbonyl group, a substituted or unsubstituted alkylcarbonyl group, a substituted or unsubstituted aryl carbonyl group, amide group, a substituted or unsubstituted monoalkylaminocarbonyl group, a substituted or unsubstituted dialkylaminocarbonyl group, a substituted or unsubstituted monoarylaminocarbonyl group, a substituted or unsubstituted diarylaminocarbonyl group, sulfonic acid group, a substituted or unsubstituted alkoxysulfonyl group, a substituted or unsubstituted aryloxysulfonyl group, a substituted or unsubstituted alkylsulfonyl group, a substituted or unsubstituted arylsulfonyl group, sulfoneamide group, a substituted or unsubstituted monoalkylaminosulfonyl group, a substituted or unsubstituted dialkylaminosulfonyl group, a substituted or unsubstituted monoarylaminosulfonyl group, a substituted or unsubstituted diarylaminosulfonyl group, amino group, a substituted or unsubstituted monoalkylamino group, a substituted or unsubstituted dialkyl amino group, a substituted or unsubstituted alkyl group, a substituted or unsubstituted alkenyl group, a substituted or unsubstituted alkynyl group, a substituted or unsubstituted aryl group, a substituted or unsubstituted alkoxy group, a substituted or unsubstituted aryloxy group, a substituted or unsubstituted alkylthio group, a substituted or unsubstituted arylthio group, and a substituted or unsubstituted heterocyclic group.

Among these groups, alkyl group, alkoxy group, hydrogen atom, aryl group, aryloxy group, halogen atom, alkenyl group, and alkynyl group are preferred, for stable operation.

Specific examples of the halogen atom include, but are not limited to, fluorine atom, chlorine atom, bromine atom, and iodine atom.

Specific examples of the alkyl group include, but are not limited to, methyl group, ethyl group, propyl group, and butyl group.

Specific examples of the aryl group include, but are not limited to, phenyl group and naphthyl group.

Specific examples of the aralkyl group include, but are not limited to, benzyl group, phenethyl group, and naphthylmethyl group.

Specific examples of the alkoxy group include, but are not limited to, methoxy group, ethoxy group, and propoxy group.

Specific examples of the aryloxy group include, but are not limited to, phenoxy group, 1-naphthyloxy group, 2-naphthyloxy group, 4-methoxyphenoxy group, and 4-methylphenoxy group.

Specific examples of the heterocyclic group include, but are not limited to, carbazole, dibenzofuran, dibenzothiophene, oxadiazole, and thiadiazole.

The substituent may be further substituted with a substituent, such as a halogen atom, nitro group, cyano group, an alkyl group (e.g., methyl group, ethyl group), an alkoxy group (e.g., methoxy group, ethoxy group), an aryloxy group (e.g., phenoxy group), an aryl group (e.g., phenyl group, naphthyl group), and an aralkyl group (e.g., benzyl group, phenethyl group).

Radical Polymerizable Functional Group

The radical polymerizable functional group refers to a radical polymerizable group having a carbon-carbon double bond.

Specific examples of the radical polymerizable functional group include, but are not limited to, 1-substituted ethylene functional groups and 1,1-substituted ethylene functional groups described below.

(1) Specific examples of the 1-substituted ethylene functional groups include, but are not limited to, a functional group represented by the following general formula (i).

$$CH_2=CH-X_1 \qquad \text{[General Formula (i)]}$$

In the general formula (i), $X_1$ represents a substituted or unsubstituted arylene group, a substituted or unsubstituted alkenylene group, —CO— group, —COO— group, or —CON($R_{100}$)— group (where $R_{100}$ represents a hydrogen atom, an alkyl group, an aralkyl group, or an aryl group), or —S— group.

Specific examples of the arylene group in the general formula (i) include, but are not limited to, a substituted or unsubstituted phenylene group and naphthylene group.

Specific examples of the alkenylene group include, but are not limited to, ethenylene group, propenylene group, and butenylene group.

Specific examples of the alkyl group include, but are not limited to, methyl group and ethyl group.

Specific examples of the aralkyl group include, but are not limited to, benzyl group, naphthylmethyl group, and phenethyl group.

Specific examples of the aryl group include, but are not limited to, phenyl group and naphthyl group.

Specific examples of the radical polymerizable functional group represented by the general formula (i) include, but are not limited to, vinyl group, styryl group, 2-methyl-1,3-butadienyl group, vinyl carbonyl group, acryloyloxy group, acryloylamide group, and vinyl thioether group.

(2) Specific examples of the 1,1-substituted ethylene functional groups include, but are not limited to, a functional group represented by the following general formula (ii).

$$CH_2=C(Y)-X_2- \qquad \text{[General Formula (ii)]}$$

In the general formula (ii), Y represents a substituted or unsubstituted alkyl group, a substituted or unsubstituted aralkyl group, a substituted or unsubstituted aryl group, a halogen atom, cyano group, nitro group, an alkoxy group, or —COOR$_{101}$ group (where R$_{101}$ represents a hydrogen atom, a substituted or unsubstituted alkyl group, a substituted or unsubstituted aralkyl group, a substituted or unsubstituted aryl group, or CONR$_{102}$R$_{103}$ (where each of R$_{102}$ and R$_{103}$ independently represents a hydrogen atom, a substituted or unsubstituted alkyl group, a substituted or unsubstituted aralkyl group, or a substituted or unsubstituted aryl group)). X$_2$ represents a substituent such as those of X$_1$ in the general formula (i), a single bond, or an alkylene group. At least one of Y and X$_2$ represents oxycarbonyl group, cyano group, an alkenylene group, or an aromatic ring.

Specific examples of the aryl group in the general formula (ii) include, but are not limited to, phenyl group and naphthyl group.

Specific examples of the alkyl group include, but are not limited to, methyl group and ethyl group.

Specific examples of the alkoxy group include, but are not limited to, methoxy group and ethoxy group.

Specific examples of the aralkyl group include, but are not limited to, benzyl group, naphthylmethyl group, and phenethyl group.

Specific examples of the radical polymerizable functional group represented by the general formula (ii) include, but are not limited to, α-acryloyloxy chloride group, methacryloyloxy group, α-cyanoethylene group, a-cyanoacryloyloxy group, α-cyanophenylene group, and methacryloyl amino group.

$X_1$, $X_2$, and Y may be further substituted with a substituent, such as a halogen atom, nitro group, cyano group, an alkyl group (e.g., methyl group, ethyl group), an alkoxy group (e.g., methoxy group, ethoxy group), an aryloxy group (e.g., phenoxy group), an aryl group (e.g., phenyl group, naphthyl group), and an aralkyl group (e.g., benzyl group, phenethyl group).

In particular, acryloyloxy group and methacryloyloxy group are preferred as the radical polymerizable functional group.

Specific preferred examples of the triaryl amine-containing radical polymerizable compound include compounds represented by the following general formulae 1-1 to 1-3.

[General Formula 1-1]

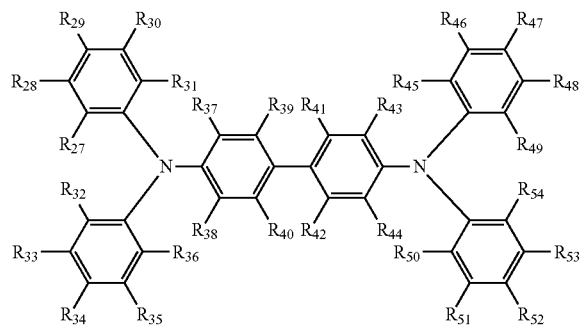

[General Formula 1-2]

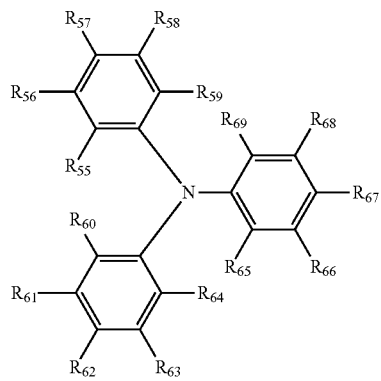

[General Formula 1-3]

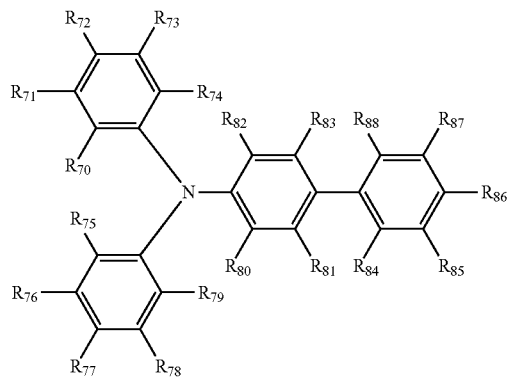

In the general formulae 1-1 to 1-3, each of $R_{27}$ to $R_{88}$ independently represents a monovalent organic group, and at least one of the monovalent organic groups is a radical polymerizable functional group.

Specific examples of the monovalent organic group and the radical polymerizable functional group include those in the general formulae 2 and 3.

Specific examples of the compounds represented by any of the general formulae 1 and 1-1 to 1-3 include the following example compounds, but are not limited thereto. The triarylamine-containing radical polymerizable compound is not limited to these compounds.

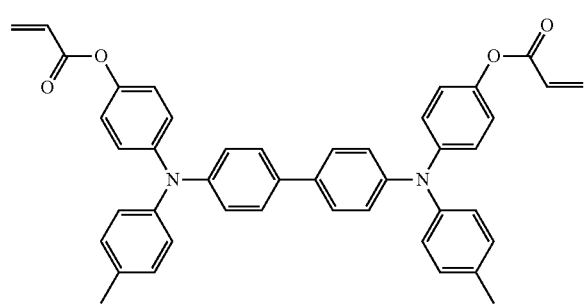

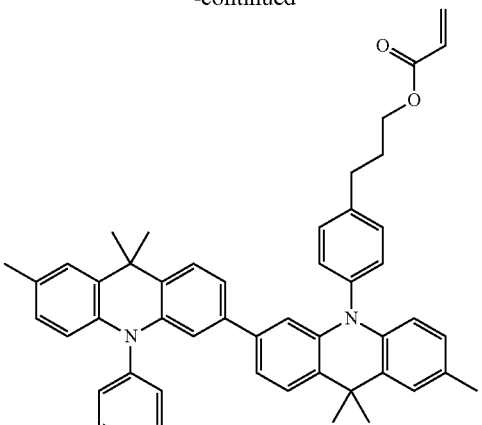

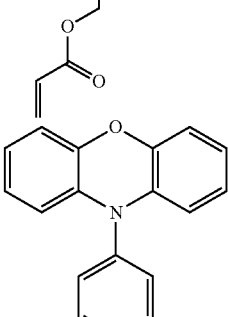
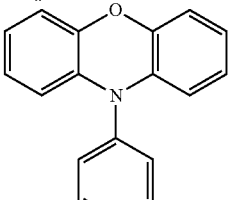
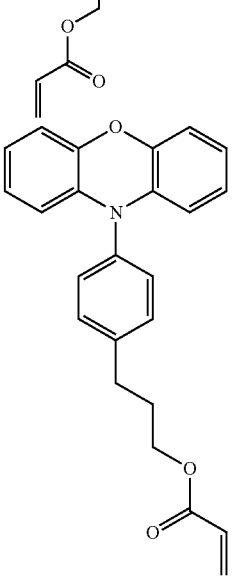

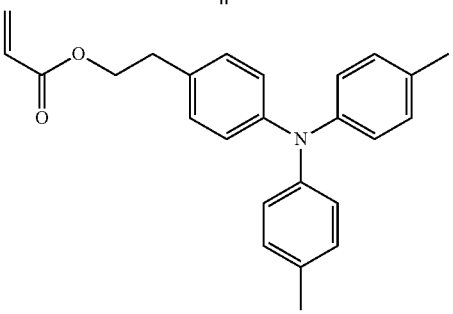

Furthermore, a cross-linked product of an electrochromic material (composition) comprising a radical polymerizable compound having a triarylamine structure represented by the general formula 1 and another radical polymerizable compound different from the radical polymerizable compound having a triarylamine structure is preferable for further improving dissolution resistance and durability of the polymer. Examples of the another radical polymerizable compound mixed in the composition include, but are not limited to, compounds having a diarylamine structure (diarylamine compounds), (meth)acrylate compounds, di(meth)acrylate compounds, tri(meth)acrylate compounds, (meth)acrylate compounds having an ethylene oxide group, di(meth)acrylate compounds having an ethylene oxide group, and tri(meth)acrylate compounds having an ethylene oxide group.

Preferably, the electrochromic layer containing a compound having a triarylamine backbone represented by the above general formula 1 is formed by forming a coated film with a coating liquid in which a composition containing the compound having a triarylamine backbone represented by the above general formula 1, another radical polymerizable compound, and optionally other components is dissolved in a solvent and then polymerizing the coated film with light and heat.

Examples of the other components include, but are not limited to, a polymerization initiator, a solvent, a plasticizer, a leveling agent, a sensitizer, a dispersant, a surfactant, an antioxidant, and a filler.

The coating method may be, for example, spin coating, casting, micro gravure coating, gravure coating, bar coating, roll coating, wire bar coating, dip coating, slit coating, capillary coating, spray coating, or nozzle coating, or various printing methods such as gravure printing, screen printing, flexo printing, offset printing, reverse printing, and inkjet printing.

The thickness of the electrochemical reaction layer is not particularly limited and can be appropriately selected according to the purpose, but is preferably from 0.2 to 5.0 µm.

When the thickness is less than 0.2 µm, coloring density may be insufficient. When the thickness is greater than 5.0 µm, manufacturing cost may increase and visibility may decrease due to haze and coloring.

The electrochromic element (cell) according to an embodiment of the present invention has a structure in which a display substrate and a counter substrate are bonded to each other with a space therebetween. An electrolyte layer containing an electrolyte layer material is disposed inside the cell (for example, the cell is filled with an electrolytic solution).

Electrolyte Layer

The electrolyte layer transfers charge by moving ions between the display electrode and the counter electrode to cause coloring/decoloring reactions of the electrochromic layer.

Examples of the electrolyte layer material include, but are not limited to: inorganic ion salts such as alkali metal salts and alkali-earth metal salts; quaternary ammonium salts; and supporting salts of acids and bases.

Specific examples thereof include, but are not limited to, $LiClO_4$, $LiBF_4$, $LiAsF_6$, $LiPF_6$, $LiCF_3SO_3$, $LiCF_3COO$, $KCl$, $NaClO_3$, $NaCl$, $NaBF_4$, $NaSCN$, $KBF_4$, $Mg(ClO_4)_2$, and $Mg(BF_4)_2$.

In addition, ionic liquids can also be used. In particular, organic ionic liquids include compounds having a molecular structure which exhibits liquidity in a wide temperature range including room temperature.

In such a molecular structure exhibiting liquidity, the cationic component may be, for example: an imidazole derivative such as N,N-dimethylimidazole salt, N,N-methylethylimidazole salt, and N,N-methylpropylimidazole salt; a pyridinium derivative such as N,N-dimethylpyridinium salt and N,N-methylpropylpyridinium salt; an aromatic salt; a tetraalkylammonium such as trimethylpropylammonium salt, trimethylhexylammonium salt, and triethylhexylammonium salt; or an aliphatic quaternary ammonium salt.

On the other hand, for stability in the atmosphere, the anionic component is preferably a fluorine-containing compound such as $BF_4^-$, $CF_3SO_3^-$, $PF_4^-$, and $(CF_3SO_2)_2N^-$. Ionic liquids prepared by combining these cationic and anionic components are preferable.

These electrolyte layer materials may be dissolved in a solvent to become an electrolytic solution and be used for the electrolyte layer.

Specific examples of the solvent include, but are not limited to, propylene carbonate, acetonitrile, γ-butyrolactone, ethylene carbonate, sulfolane, dioxolan, tetrahydrofuran, 2-methyltetrahydrofuran, dimethylsulfoxide, 1,2-dimethoxyethane, 1,2-ethoxymethoxyethane, polyethylene glycol, alcohols, and mixed solvents thereof.

The electrolytic solution can be formed into a gel or solid. This property is preferable for improving element strength and reliability and preventing diffusion of color development.

The electrolyte and the solvent are preferably held in a resin (polymer) for solid strength while maintaining high ion conductivity. The resin (polymer) is preferably a resin capable of photo-curing (photocurable resin). Compared to a method of forming a thin electrolyte layer containing a resin and an electrolyte layer material by thermal polymerization or evaporation of solvent, the use of a photocurable resin is more advantageous in that the element can be manufactured at a low temperature and in a short time.

As described above, one type of electrolyte alone or two or more types of electrolytes may be used in combination.

Preferably, the thickness of the electrolyte layer is from 0.5 to 100 µm, more preferably from 1 to 50 µm. When the thickness of the electrolyte layer is larger than 50 µm, charge is easily diffused. When the thickness of the electrolyte layer is less than 1 µm, it becomes difficult to maintain the function as the electrolyte.

Other Layers

The other layers are not particularly limited and can be appropriately selected according to the purpose. Examples thereof include, but are not limited to, an insulating porous layer and a protective layer.

Insulating Porous Layer

The insulating porous layer has a function of electrically insulating the first electrode and the second electrode from each other and another function of holding the electrolyte.

The material of the insulating porous layer is not particularly limited as long as it is transparent and porous. Preferred examples thereof include an organic material, an inorganic material, and a composite material thereof which have high insulating property and durability and excellent film formation property.

Protective Layer

The protective layer has functions of protecting the element from external stress and chemicals used in the washing process, preventing leakage of the electrolyte, and preventing intrusion of substances unnecessary for stable operation of the electrochromic element such as moisture and oxygen in the air.

The average thickness of the protective layer is not particularly limited and can be appropriately selected according to the purpose, but is preferably from 1 to 200 µm.

Examples of the material of the protective layer include, but are not limited to, ultraviolet-curable and heat-curable resins such as acrylic resin, urethane resin, and epoxy resin.

Next, the electrochromic element according to an embodiment of the present invention is described with reference to the drawing. The electrochromic element 10 includes a first substrate 1a, a first electrode 2a overlying the first substrate 1a, a second substrate 1b disposed at a distance from the first electrode 2a, a second electrode 2b overlying the second substrate 1b, a first electrochemical reaction layer 3a in contact with the first electrode 2a, a second electrochemical reaction layer 3b in contact with the second electrode 2b, and an electrolyte layer 4 between the first electrode 2a and the second electrode 2b.

Method for Manufacturing Electrochromic Element

The method for manufacturing an electrochromic element according to an embodiment of the present invention is a method for manufacturing the electrochromic element according to an embodiment of the present invention, that includes an oxidation treatment process and optionally other processes as required.

Oxidation Treatment Process

The oxidation treatment process is a process of oxidizing at least one of the first electrochemical reaction layer and the second electrochemical reaction layer.

By oxidizing at least one of the first electrochemical reaction layer and the second electrochemical reaction layer, at least one of the first electrochemical reaction layer and the second electrochemical reaction layer can be kept in a radical cation state.

The oxidation treatment may be performed by, for example, disposing electrically-conductive electrodes, such as metal foils, opposite to each other via an electrolytic solution and applying a voltage thereto to put the electrochemical reaction layer in a radical cation state.

The method for manufacturing an electrochromic element is not particularly limited as long as the above-described oxidation treatment is performed. For example, the method may further include processes of forming the first electrode and the first electrochemical reaction layer on the first substrate, forming the second electrode and the second electrochemical reaction layer on the second substrate, and bonding the first substrate and the second substrate to each other via the electrolyte layer. In a case in which the electrolyte layer is curable by light or heat, the electrolyte layer may be cured after the bonding. The outer periphery of the element may be sealed to prevent entry of moisture, oxygen, and the like.

The electrochromic element according to an embodiment of the present invention has excellent responsiveness to decoloring and is in a solid state. Therefore, the electrochromic element is suitably used for, for example, large-size displays such as electrochromic display and stock price display, light control elements such as light control lens, light control window, light shielding filter, and anti-glare mirror, low-voltage driving elements such as touch panel key switch, as well as optical switch, optical memory, electronic paper, and electronic album.

EXAMPLES

Further understanding can be obtained by reference to certain specific examples which are provided herein for the purpose of illustration only and are not intended to be limiting.

In the following examples and comparative examples, the first electrochromic layer was formed as the first electrochemical reaction layer, and the second electrochromic layer was formed as the second electrochemical reaction layer.

Example 1

An electrochromic element was prepared by the following processes (1) to (5) in accordance with the configuration illustrated in the drawing.

(1) Formation of First Electrochromic Layer on First Electrode

To form a first electrochromic layer on a first electrode, the following electrochromic composition 1 was prepared.

[Composition]

Diarylamine compound represented by the following structural formula (electrochromic compound exhibiting green color upon oxidation): 70 parts by mass

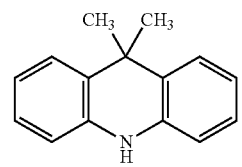

[Diarylamine Compound]

IRGACURE 184 (available from BASF Japan Ltd.): 2 parts by mass

PEG400DA containing a difunctional acrylate (polyethylene glycol diacrylate, available from Nippon Kayaku Co., Ltd.): 30 parts by mass Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 μm.

(2) Formation of Second Electrochromic Layer on Second Electrode

To form a second electrochromic layer on a second electrode, the following electrochromic composition 2 was prepared.

[Composition]

Triarylamine compound 1 containing a difunctional acrylate represented by the following structural formula (electrochromic compound exhibiting brown color upon oxidation): 70 parts by mass

[Triarylamine Compound 1]

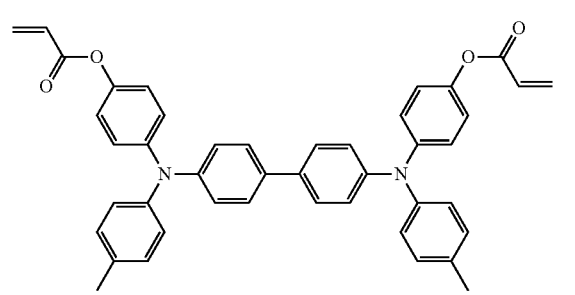

IRGACURE 184 (available from BASF Japan Ltd.): 2 parts by mass

PEG400DA containing a difunctional acrylate (polyethylene glycol diacrylate, available from Nippon Kayaku Co., Ltd.): 30 parts by mass Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

(3) Preparation of Electrolyte Solution

An electrolyte solution having the following composition was prepared.

IRGACURE 184 (available from BASF Japan Ltd.): 5 parts by mass

PEG400DA containing a difunctional acrylate (polyethylene glycol diacrylate, available from Nippon Kayaku Co., Ltd.): 100 parts by mass 1-Ethyl-3-methylimidazolium tetracyanoborate (available from Merk KGaA): 50 parts by mass (4) Oxidation Treatment of First Electrochromic Layer The electrolyte solution obtained in the process (3) was applied onto the first substrate. Since the electrochromic layer has a porous structure, the electrolyte layer material sufficiently penetrates the first electrode to reach the interface therebetween. Next, a coloring treatment substrate was temporarily bonded with the first substrate in an overlapping manner so that the electrode thereof and the side of the electrolyte layer material faced with each other. In this state, a voltage of 3.0 V was applied for 5 seconds so that the first electrode had a positive potential, and the first electrochromic layer was oxidized to be put into a colored state. Finally, the coloring treatment substrate temporarily bonded with the first substrate was separated off.

(5) Bonding

The electrolyte solution prepared in the process (3) was applied onto the first electrochromic layer on the first substrate oxidized in the process (4). Since the electrochromic layer has a porous structure, the electrolyte layer material sufficiently penetrates the first electrode to reach the interface therebetween.

Next, the second electrochromic layer formed on the second substrate was bonded with the side of the electrolyte layer material in an overlapping manner.

Immediately after the bonding, the element was irradiated with UV (wavelength of 250 nm) by a UV irradiator (SPOT CURE manufactured by Ushio Inc.) at 10 mW for 60 seconds to cross-link the electrolyte solution applied portion. Thus, an electrochromic element of Example 1 was prepared.

Subsequently, the above-prepared electrochromic element of Example 1 was subjected to the following driving test 1 and driving test 2. The results are shown in Table 3.

Driving Test 1: Color Retention Test

The above-prepared electrochromic element was connected to an external power supply so that the second electrode had a positive potential, and a voltage was applied so that a constant current of 0.7 mA flowed for 10 seconds. By this operation, a coloring driving (for coloring the second electrochromic layer and decoloring the first electrochromic layer) was attempted. Next, the first electrode and the second electrode were put into an open state, and the color retention time of the second electrochromic layer (the time required for the absorbance of the absorption peak to become ⅓ of the initial value) was recorded. Evaluation was conducted based on the following evaluation criteria.

Evaluation Criteria

A: Driven by application of voltage. The color retention time is 10 minutes or more.

B: Driven by application of voltage. The color retention time is less than 10 minutes.

C: Not driven by application of voltage.

Driving Test 2: Decoloring Driving Test

The above-prepared electrochromic element was connected to an external power supply so that the second electrode had a positive potential, and a voltage was applied so that a constant current of 0.7 mA flowed for 10 seconds.

Next, the first electrode and the second electrode were put into an open state and a colored state (in which the second electrochromic layer was colored and the first electrochromic layer was decolored) was held for 5 minutes. The electrochromic element was then connected to an external power supply so that the first electrode had a positive potential, and a voltage was applied so that a constant current of 0.7 mA flowed for 10 seconds, to conduct a decoloring driving (for coloring the first electrochromic layer and decoloring the second electrochromic layer). The element was observed during the above operations, and evaluation was conducted based on the following evaluation criteria.

Evaluation Criteria

A: The decoloring driving took less than 10 seconds to complete due to short circuit.

B: The decoloring driving took 10 seconds or more to complete due to short circuit.

C: The decoloring driving did not complete even by short circuit, and the second electrochromic layer was not completely decolored and the residual color generated.

Example 2

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.

[Composition]

Diarylamine compound represented by the above structural formula (electrochromic compound exhibiting green color upon oxidation): 70 parts by mass IRGACURE 184 (available from BASF Japan Ltd.): 2 parts by mass PEG400DA containing a difunctional acrylate (polyethylene glycol diacrylate, available from Nippon Kayaku Co., Ltd.): 30 parts by mass Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 μm.

(2) Formation of Second Electrochromic Layer on Second Electrode

To form a second electrochromic layer on a second electrode, the following electrochromic composition 2 was prepared.

[Composition]

Triarylamine compound 2 containing a difunctional acrylate represented by the following structural formula (electrochromic compound exhibiting yellow color upon oxidation): 70 parts by mass

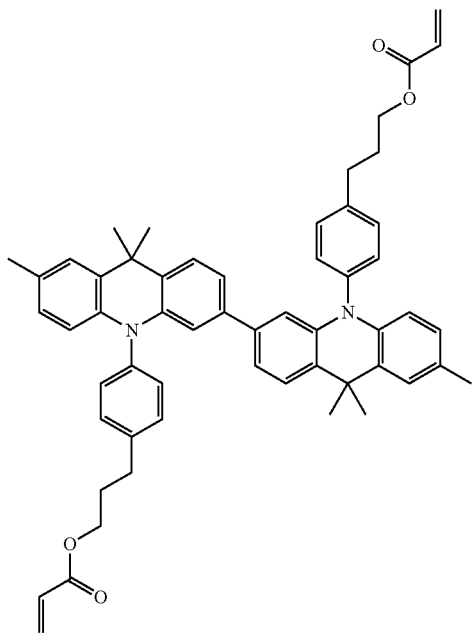

[Triarylamine Compound 2]

IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 µm.

Subsequently, the processes of (3) to (5) in Example 1 were repeated to prepare an electrochromic element of Example 2. The electrochromic element was subjected to the driving tests 1 and 2 in the same manner as in Example 1. The results are shown in Table 3.

Example 3

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.

[Composition]
Diarylamine compound represented by the above structural formula (electrochromic compound exhibiting green color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 µm.

(2) Formation of Second Electrochromic Layer on Second Electrode

To form a second electrochromic layer on a second electrode, the following electrochromic composition 2 was prepared.

[Composition]
Triarylamine compound 3 containing a monofunctional acrylate represented by the following structural formula (electrochromic compound exhibiting magenta color upon oxidation): 70 parts by mass

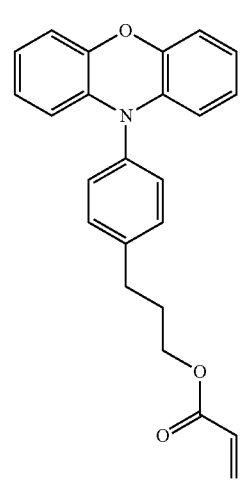

[Triarylamine Compound 3]

IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 µm.

Subsequently, the processes of (3) to (5) in Example 1 were repeated to prepare an electrochromic element of Example 3. The electrochromic element was subjected to the driving tests 1 and 2 in the same manner as in Example 1. The results are shown in Table 3.

Example 4

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.

[Composition]
Triarylamine compound 1 containing a difunctional acrylate represented by the above structural formula (electrochromic compound exhibiting brown color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 μm.

(2) Formation of Second Electrochromic Layer on Second Electrode

To form a second electrochromic layer on a second electrode, the following electrochromic composition 2 was prepared.

[Composition]
Triarylamine compound 2 containing a difunctional acrylate represented by the above structural formula (electrochromic compound exhibiting yellow color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

Subsequently, the processes of (3) to (5) in Example 1 were repeated to prepare an electrochromic element of Example 4. The electrochromic element was subjected to the driving tests 1 and 2 in the same manner as in Example 1. The results are shown in Table 3.

Example 5

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.

[Composition]
Triarylamine compound 1 containing a difunctional acrylate represented by the above structural formula (electrochromic compound exhibiting brown color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 μm.

(2) Formation of Second Electrochromic Layer on Second Electrode

To form a second electrochromic layer on a second electrode, the following electrochromic composition 2 was prepared.

[Composition]
Triarylamine compound 3 containing a monofunctional acrylate represented by the above structural formula (electrochromic compound exhibiting magenta color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

Subsequently, the processes of (3) to (5) in Example 1 were repeated to prepare an electrochromic element of Example 5. The electrochromic element was subjected to the driving tests 1 and 2 in the same manner as in Example 1. The results are shown in Table 3.

Example 6

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.

[Composition]
Triarylamine compound 2 containing a difunctional acrylate represented by the above structural formula (electrochromic compound exhibiting yellow color upon oxidation): 70 parts by mass IRGACURE 184 (available from BASF Japan Ltd.): 2 parts by mass PEG400DA containing a difunctional acrylate (polyethylene glycol diacrylate, available from Nippon Kayaku Co., Ltd.): 30 parts by mass Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 µm.

(2) Formation of Second Electrochromic Layer on Second Electrode

To form a second electrochromic layer on a second electrode, the following electrochromic composition 2 was prepared.

[Composition]

Triarylamine compound 3 containing a monofunctional acrylate represented by the above structural formula (electrochromic compound exhibiting magenta color upon oxidation): 70 parts by mass IRGACURE 184 (available from BASF Japan Ltd.): 2 parts by mass PEG400DA containing a difunctional acrylate (polyethylene glycol diacrylate, available from Nippon Kayaku Co., Ltd.): 30 parts by mass Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 µm.

Subsequently, the processes of (3) to (5) in Example 1 were repeated to prepare an electrochromic element of Example 6. The electrochromic element was subjected to the driving tests 1 and 2 in the same manner as in Example 1. The results are shown in Table 3.

Example 7

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.

[Composition]

Diarylamine compound represented by the above structural formula (electrochromic compound exhibiting green color upon oxidation): 70 parts by mass IRGACURE 184 (available from BASF Japan Ltd.): 2 parts by mass PEG400DA containing a difunctional acrylate (polyethylene glycol diacrylate, available from Nippon Kayaku Co., Ltd.): 30 parts by mass Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 µm.

(2) Formation of Second Electrochromic Layer on Second Electrode

To form a second electrochromic layer on a second electrode, the following electrochromic composition 2 was prepared.

[Composition]

Triarylamine compound 4 containing a monofunctional acrylate represented by the following structural formula (electrochromic compound exhibiting blue color upon oxidation): 70 parts by mass

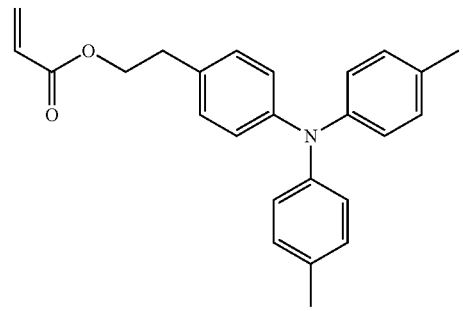

[Triarylamine Compound 4]

IRGACURE 184 (available from BASF Japan Ltd.): 2 parts by mass

PEG400DA containing a difunctional acrylate (polyethylene glycol diacrylate, available from Nippon Kayaku Co., Ltd.): 30 parts by mass Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 µm.

Subsequently, the processes of (3) to (5) in Example 1 were repeated to prepare an electrochromic element of Example 7. The electrochromic element was subjected to the driving tests 1 and 2 in the same manner as in Example 1. The results are shown in Table 3.

Example 8

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.

[Composition]

Diarylamine compound represented by the above structural formula (electrochromic compound exhibiting green color upon oxidation): 70 parts by mass IRGACURE 184 (available from BASF Japan Ltd.): 2 parts by mass PEG400DA containing a difunctional acrylate (polyethylene glycol diacrylate, available from Nippon Kayaku Co., Ltd.): 30 parts by mass Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 µm.

(2) Formation of Second Electrochemical Reaction Layer on Second Electrode

To form a second electrochemical reaction layer on a second electrode, a tin oxide dispersion liquid having the following composition was prepared.

[Composition]

Tin oxide particles: 45 parts by mass

HW140SF (available from DIC Corporation): 49 parts by mass

Tetrafluoropropanol: 906 parts by mass

The above-prepared tin oxide dispersion liquid was applied onto an ITO glass substrate (having an area of 40 mm×40 mm, a thickness of 0.7 mm, and an ITO film thickness of about 100 nm) as the first electrode by spin coating and annealed at 90 degrees C. for 15 minutes to form a tin oxide particle film.

(3) Preparation of Electrolyte Solution

An electrolyte solution having the following composition was prepared.

IRGACURE 184 (available from BASF Japan Ltd.): 5 parts by mass

PEG400DA containing a difunctional acrylate (polyethylene glycol diacrylate, available from Nippon Kayaku Co., Ltd.): 100 parts by mass 1-Ethyl-3-methylimidazolium tetracyanoborate (available from Merk KGaA): 50 parts by mass (4) Bonding The electrolyte solution prepared in the process (3) was applied onto the first electrochromic layer on the first substrate. Since the first electrochromic layer has a porous structure, the electrolyte layer material sufficiently penetrates the first electrode to reach the interface therebetween.

Next, the second electrochemical reaction layer formed on the second substrate was bonded with the side of the electrolyte layer material in an overlapping manner.

Immediately after the bonding, the element was irradiated with UV (wavelength of 250 nm) by a UV irradiator (SPOT CURE manufactured by Ushio Inc.) at 10 mW for 60 seconds to cross-link the electrolyte solution applied portion. Thus, an electrochromic element of Example 8 was prepared.

The electrochromic element was subjected to the driving tests 1 and 2 in the same manner as in Example 1. The results are shown in Table 3.

Example 9

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.

[Composition]

Triarylamine compound 1 containing a difunctional acrylate represented by the above structural formula (electrochromic compound exhibiting yellow color upon oxidation): 70 parts by mass IRGACURE 184 (available from BASF Japan Ltd.): 2 parts by mass PEG400DA containing a difunctional acrylate (polyethylene glycol diacrylate, available from Nippon Kayaku Co., Ltd.): 30 parts by mass Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 µm.

(2) Formation of Second Electrochemical Reaction Layer on Second Electrode

To form a second electrochemical reaction layer on a second electrode, a tin oxide dispersion liquid having the following composition was prepared.

[Composition]

Tin oxide particles: 45 parts by mass

HW140SF (available from DIC Corporation): 49 parts by mass

Tetrafluoropropanol: 906 parts by mass

The above-prepared tin oxide dispersion liquid was applied onto an ITO glass substrate (having an area of 40 mm×40 mm, a thickness of 0.7 mm, and an ITO film thickness of about 100 nm) as the first electrode by spin coating and annealed at 90 degrees C. for 15 minutes to form a tin oxide particle film.

(3) Preparation of Electrolyte Solution

An electrolyte solution having the following composition was prepared.

IRGACURE 184 (available from BASF Japan Ltd.): 5 parts by mass

PEG400DA containing a difunctional acrylate (polyethylene glycol diacrylate, available from Nippon Kayaku Co., Ltd.): 100 parts by mass 1-Ethyl-3-methylimidazolium tetracyanoborate (available from Merk KGaA): 50 parts by mass (4) Bonding The electrolyte solution prepared in the process (3) was applied onto the first electrochromic layer on the first substrate. Since the first electrochromic layer has a porous structure, the electrolyte layer material sufficiently penetrates the first electrode to reach the interface therebetween.

Next, the second electrochemical reaction layer formed on the second substrate was bonded with the side of the electrolyte layer material in an overlapping manner.

Immediately after the bonding, the element was irradiated with UV (wavelength of 250 nm) by a UV irradiator (SPOT CURE manufactured by Ushio Inc.) at 10 mW for 60 seconds to cross-link the electrolyte solution applied portion. Thus, an electrochromic element of Example 8 was prepared.

The electrochromic element was subjected to the driving tests 1 and 2 in the same manner as in Example 1. The results are shown in Table 3.

Comparative Example 1

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.

[Composition]
Diarylamine compound represented by the above structural formula (electrochromic compound exhibiting green color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method. The applied film was irradiated by an UV irradiator (SPOT CURE manufactured by Ushio Inc.) at 10 mW for 60 seconds to form the cross-linked first electrochromic layer having an average thickness of 1.0 μm.

(2) Formation of Second Electrochromic Layer on Second Electrode

To form a second electrochromic layer on a second electrode, the following electrochromic composition 2 was prepared.

[Composition]
Triarylamine compound 1 containing a difunctional acrylate represented by the above structural formula (electrochromic compound exhibiting yellow color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

(3) Preparation of Electrolyte Solution

An electrolyte solution having the following composition was prepared.
IRGACURE 184 (available from BASF Japan Ltd.): 5 parts by mass
PEG400DA containing a difunctional acrylate (polyethylene glycol diacrylate, available from Nippon Kayaku Co., Ltd.): 100 parts by mass
1-Ethyl-3-methylimidazolium tetracyanoborate (available from Merk KGaA): 50 parts by mass (4) Bonding The electrolyte solution prepared in the process (3) was applied onto the first electrochromic layer on the first substrate. Since the first electrochromic layer has a porous structure, the electrolyte layer material sufficiently penetrates the first electrode to reach the interface therebetween.

Next, the second electrochromic layer formed on the second substrate was bonded with the side of the electrolyte layer material in an overlapping manner.

Immediately after the bonding, the element was irradiated with UV (wavelength of 250 nm) by a UV irradiator (SPOT CURE manufactured by Ushio Inc.) at 10 mW for 60 seconds to cross-link the electrolyte solution applied portion. Thus, an electrochromic element of Comparative Example 1 was prepared.

The electrochromic element was subjected to the driving tests 1 and 2 in the same manner as in Example 1. The results are shown in Table 3.

Comparative Example 2

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.

[Composition]
Diarylamine compound represented by the above structural formula (electrochromic compound exhibiting green color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 μm.

(2) Formation of Second Electrochromic Layer on Second Electrode

To form a second electrochromic layer on a second electrode, the following electrochromic composition 2 was prepared.

[Composition]
Triarylamine compound 2 containing a difunctional acrylate represented by the above structural formula (electrochromic compound exhibiting yellow color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

Subsequently, the processes of (3) to (4) in Comparative Example 1 were repeated to prepare an electrochromic element of Comparative Example 2. The electrochromic element was subjected to the driving tests 1 and 2 in the same manner as in Example 1. The results are shown in Table 3.

Comparative Example 3

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.
[Composition]
Diarylamine compound represented by the above structural formula (electrochromic compound exhibiting green color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 μm.

(2) Formation of Second Electrochromic Layer on Second Electrode

To form a second electrochromic layer on a second electrode, the following electrochromic composition 2 was prepared.
[Composition]
Triarylamine compound 3 containing a monofunctional acrylate represented by the above structural formula (electrochromic compound exhibiting magenta color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

Subsequently, the processes of (3) to (4) in Comparative Example 1 were repeated to prepare an electrochromic element of Comparative Example 3. The electrochromic element was subjected to the driving tests 1 and 2 in the same manner as in Example 1. The results are shown in Table 3.

Comparative Example 4

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.
[Composition]
Triarylamine compound 1 containing a difunctional acrylate represented by the above structural formula (electrochromic compound exhibiting brown color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 μm.

(2) Formation of Second Electrochromic Layer on Second Electrode

To form a second electrochromic layer on a second electrode, the following electrochromic composition 2 was prepared.
[Composition]
Triarylamine compound 2 containing a difunctional acrylate represented by the above structural formula (electrochromic compound exhibiting yellow color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

Subsequently, the processes of (3) to (4) in Comparative Example 1 were repeated to prepare an electrochromic element of Comparative Example 4. The electrochromic element was subjected to the driving tests 1 and 2 in the same manner as in Example 1. The results are shown in Table 3.

Comparative Example 5

An electrochromic element having the configuration illustrated in the drawing was produced by the following procedure.

(1) Formation of First Electrochromic Layer on First Electrode

To form a first electrochromic layer on a first electrode, the following electrochromic composition 1 was prepared.

[Composition]
Triarylamine compound 1 containing a difunctional acrylate represented by the above structural formula (electrochromic compound exhibiting brown color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 μm.

(2) Formation of Second Electrochromic Layer on Second Electrode

To form a second electrochromic layer on a second electrode, the following electrochromic composition 2 was prepared.

[Composition]
Triarylamine compound 3 containing a monofunctional acrylate represented by the above structural formula (electrochromic compound exhibiting magenta color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

Subsequently, the processes of (3) to (4) in Comparative Example 1 were repeated to prepare an electrochromic element of Comparative Example 5. The electrochromic element was subjected to the driving tests 1 and 2 in the same manner as in Example 1. The results are shown in Table 3.

Comparative Example 6

An electrochromic element having the configuration illustrated in the drawing was produced by the following procedure.

(1) Formation of First Electrochromic Layer on First Electrode

To form a second electrochromic layer on a first electrode, the following electrochromic composition 1 was prepared.

[Composition]
Triarylamine compound 2 containing a difunctional acrylate represented by the above structural formula (electrochromic compound exhibiting yellow color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 1 was applied onto an ITO glass substrate (having an area of 40 mm×40 mm, a thickness of 0.7 mm, and an ITO film thickness of about 100 nm) as the first electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked first electrochromic layer having an average thickness of 1.0 μm.

(2) Formation of Second Electrochromic Layer on Second Electrode

To form an electrochromic layer on a second electrode, the following electrochromic composition 2 was prepared.

[Composition]
Triarylamine compound 3 containing a monofunctional acrylate represented by the above structural formula (electrochromic compound exhibiting magenta color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

Subsequently, the processes of (3) to (4) in Comparative Example 1 were repeated to prepare an electrochromic element of Comparative Example 6. The electrochromic element was subjected to the driving tests 1 and 2 in the same manner as in Example 1. The results are shown in Table 3.

Comparative Example 7

An electrochromic element having the configuration illustrated in the drawing was produced by the following procedure.

(1) Formation of First Electrochromic Layer on First Electrode

To form a first electrochromic layer on a first electrode, a titanium oxide particle dispersion (SP210 manufactured by Showa Titanium Co., Ltd.) was applied onto an ITO glass substrate (having an area of 40 mm×40 mm, a thickness of 0.7 mm, and an ITO film thickness of about 100 nm) by spin coating and annealed at 120 degrees C. for 15 minutes to form a titanium oxide particle film.

Subsequently, a 2,2,3,3-tetrafluoropropanol solution containing 2% by mass of a viologen compound represented by the following structural formula, which is an electrochromic compound that exhibits blue color, was dropped thereon and soaked for 1 minute, and then annealed at 120 degrees C. for 10 minutes to form a first electrochromic layer having an average thickness of 1.0 μm.

[Viologen Compound]

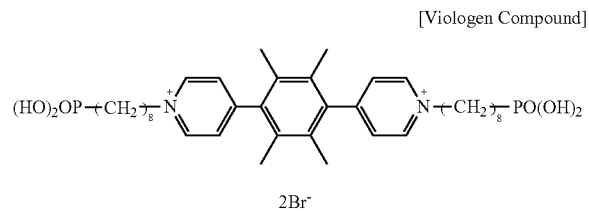

2Br⁻

(2) Formation of Second Electrochromic Layer on Second Electrode

To form a second electrochromic layer on a second electrode, the following electrochromic composition 2 was prepared.

[Composition]
Triarylamine compound 1 containing a difunctional acrylate represented by the above structural formula (electrochromic compound exhibiting brown color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

Subsequently, the processes of (3) to (4) in Comparative Example 1 were repeated to prepare an electrochromic element of Comparative Example 7. The electrochromic element was subjected to the driving tests 1 and 2 in the same manner as in Example 1. The results are shown in Table 3.

Comparative Example 8

An electrochromic element having the configuration illustrated in the drawing was produced by the following procedure.

(1) Formation of First Electrochromic Layer on First Electrode

To form a first electrochromic layer on a first electrode, a titanium oxide particle dispersion (SP210 manufactured by Showa Titanium Co., Ltd.) was applied onto an ITO glass substrate (having an area of 40 mm×40 mm, a thickness of 0.7 mm, and an ITO film thickness of about 100 nm) by spin coating and annealed at 120 degrees C. for 15 minutes to form a titanium oxide particle film.

Subsequently, a 2,2,3,3-tetrafluoropropanol solution containing 2% by mass of a viologen compound represented by the above structural formula, which is an electrochromic compound that exhibits blue color, was dropped thereon and soaked for 1 minute, and then annealed at 120 degrees C. for 10 minutes to form a first electrochromic layer having an average thickness of 1.0 μm.

(2) Formation of Second Electrochromic Layer on Second Electrode

To form a second electrochromic layer on a second electrode, the following electrochromic composition 2 was prepared.

[Composition]
Triarylamine compound 2 containing a difunctional acrylate represented by the above structural formula (electrochromic compound exhibiting yellow color upon oxidation): 70 parts by mass
IRGACURE 184 (available from BASF Japan Ltd.): 2 parts by mass
PEG400DA containing a difunctional acrylate (polyethylene glycol diacrylate, available from Nippon Kayaku Co., Ltd.): 30 parts by mass
Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

Subsequently, the processes of (3) to (4) in Comparative Example 1 were repeated to prepare an electrochromic element of Comparative Example 8. The electrochromic element was subjected to the driving tests 1 and 2 in the same manner as in Example 1. The results are shown in Table 3.

Comparative Example 9

An electrochromic element having the configuration illustrated in the drawing was produced by the following procedure.

(1) Formation of First Electrochromic Layer on First Electrode

To form a first electrochromic layer on a first electrode, a titanium oxide particle dispersion (SP210 manufactured by Showa Titanium Co., Ltd.) was applied onto an ITO glass substrate (having an area of 40 mm×40 mm, a thickness of 0.7 mm, and an ITO film thickness of about 100 nm) by spin coating and annealed at 120 degrees C. for 15 minutes to form a titanium oxide particle film.

Subsequently, a 2,2,3,3-tetrafluoropropanol solution containing 2% by mass of a viologen compound represented by the above structural formula, which is an electrochromic compound that exhibits blue color, was dropped thereon and soaked for 1 minute, and then annealed at 120 degrees C. for 10 minutes to form a first electrochromic layer having an average thickness of 1.0 μm.

(2) Formation of Second Electrochromic Layer on Second Electrode

To form a second electrochromic layer on a second electrode, the following electrochromic composition 2 was prepared.

[Composition]
Triarylamine compound 3 containing a monofunctional acrylate represented by the above structural formula (electrochromic compound exhibiting magenta color upon oxidation): 70 parts by mass IRGACURE 184 (available from BASF Japan Ltd.): 2 parts by mass PEG400DA containing a difunctional acrylate (polyethylene glycol diacrylate, available from Nippon Kayaku Co., Ltd.): 30 parts by mass Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

Subsequently, the processes of (3) to (4) in Comparative Example 1 were repeated to prepare an electrochromic element of Comparative Example 9. The electrochromic element was subjected to the driving tests 1 and 2 in the same manner as in Example 1. The results are shown in Table 3.

Comparative Example 10

An electrochromic element having the configuration illustrated in the drawing was produced by the following procedure.

(1) Formation of First Electrochromic Layer on First Electrode

To form a first electrochromic layer on a first electrode, a titanium oxide particle dispersion (SP210 manufactured by Showa Titanium Co., Ltd.) was applied onto an ITO glass substrate (having an area of 40 mm×40 mm, a thickness of 0.7 mm, and an ITO film thickness of about 100 nm) by spin coating and annealed at 120 degrees C. for 15 minutes to form a titanium oxide particle film.

Subsequently, a 2,2,3,3-tetrafluoropropanol solution containing 2% by mass of a viologen compound represented by the above structural formula, which is an electrochromic compound that exhibits blue color, was dropped thereon and soaked for 1 minute, and then annealed at 120 degrees C. for 10 minutes to form a first electrochromic layer having an average thickness of 1.0 μm.

(2) Formation of Second Electrochromic Layer on Second Electrode

To form a second electrochromic layer on a second electrode, the following electrochromic composition 2 was prepared.

[Composition]

Diarylamine compound represented by the above structural formula (electrochromic compound exhibiting green color upon oxidation): 70 parts by mass IRGACURE 184 (available from BASF Japan Ltd.): 2 parts by mass PEG400DA containing a difunctional acrylate (polyethylene glycol diacrylate, available from Nippon Kayaku Co., Ltd.): 30 parts by mass Cyclohexanone: 600 parts by mass The electrochromic composition 2 was applied onto an ITO glass substrate (having an area of 40 mm×40 mm, a thickness of 0.7 mm, and an ITO film thickness of about 100 nm) as the second electrode into a solid shape of 30 mm×30 mm by an inkjet printing method.

The applied film was irradiated by an UV irradiator (SPOT CURE manufactured by Ushio Inc.) at 10 mW for 60 seconds to form the cross-linked second electrochromic layer having an average thickness of 1.0 μm.

Subsequently, the processes of (3) to (4) in Comparative Example 1 were repeated to prepare an electrochromic element of Comparative Example 10.

The electrochromic element was subjected to the driving tests 1 and 2 in the same manner as in Example 1. The results are shown in Table 3.

Table 1 shows the configurations of the devices manufactured in the Examples and Comparative Examples and the oxidation-reduction potential of each electrochromic layer as an electrochemical reaction layer. The oxidation-reduction potential was measured as follows.

Table 2 shows the presence or absence of the reversibly oxidizable state and the reversibly reducible state of each of the first electrochemical reaction layer and the second electrochemical reaction layer of the above-prepared devices.

Measurement of Oxidation-Reduction Potential

A cell was assembled using the following members, and cyclic voltammetry was performed under the following measurement conditions to measure the oxidation-reduction potential.

Cell Members

Working electrode: Pt electrode

Counter electrode: Pt wire

Reference electrode: Ag/Ag$^+$ (internal electrolyte: 0.1M tetrabutylammonium perchlorate (TBAP)+0.05M silver nitrate acetonitrile solution)

Solution: 0.1M TBAP acetonitrile solution (or dichloromethane solution when insoluble)

Measurement Conditions

Sweep speed: 0.05 V/s

Sweep range: −0.3 to +1.0 V

An oxidation-reduction potential E based on Ag/Ag' was determined by the formula $(E_a+E_b)/2=E$, where $E_a$ and $E_b$ represent respective potentials at which two peaks in a V-I curve obtained in the above measurement are present.

Next, under the same conditions, an oxidation-reduction potential of ferrocene was measured, and this value determined by ferrocene was used as the reference potential (0 V vs. Fc/Fc$^+$).

When tin oxide was used as the electrochemical reaction layer, since tin oxide was insoluble in a solution, CV was measured with an ITO electrode on which a solid film of tin oxide was formed as a working electrode. In the measurement of the solid film, the oxidation-reduction potential may not be obtained as a clear peak, so an intermediate value between the reduction onset potential and the oxidation end potential is defined as the oxidation-reduction potential in the present disclosure.

In addition, when a material insoluble in a solution, other than tin oxide, is used for electrochemical reaction layers, the oxidation-reduction potential may be measured by the same method.

TABLE 1

| | First Electrochromic Layer (First Electrochemical Reaction Layer) | Second Electrochromic Layer (Second Electrochemical Reaction Active Layer) | Oxidation Treatment | E1/V (vs. Fc/Fc$^+$) | E2/V (vs. Fc/Fc$^+$) | ΔE/V |
|---|---|---|---|---|---|---|
| Example 1 | Diarylamine Compound | Triarylamine Compound 1 | Yes | 0 | 0.2 | 0.2 |
| Example 2 | Diarylamine Compound | Triarylamine Compound 2 | Yes | 0 | 0.3 | 0.3 |
| Example 3 | Diarylamine Compound | Triarylamine Compound 3 | Yes | 0 | 0.3 | 0.3 |
| Example 4 | Triarylamine Compound 1 | Triarylamine Compound 2 | Yes | 0.2 | 0.3 | 0.1 |
| Example 5 | Triarylamine Compound 1 | Triarylamine Compound 3 | Yes | 0.2 | 0.3 | 0.1 |
| Example 6 | Triarylamine Compound 2 | Triarylamine Compound 3 | Yes | 0.3 | 0.3 | 0 |
| Example 7 | Diarylamine Compound | Triarylamine Compound 4 | Yes | 0 | 0.5 | 0.5 |
| Example 8 | Diarylamine Compound | Tin Oxide | No | 0 | −0.6 | 0.6 |
| Example 9 | Triarylamine Compound 1 | Tin Oxide | No | 0.2 | −0.6 | 0.8 |
| Comparative Example 1 | Diarylamine Compound | Triarylamine Compound 1 | No | 0 | 0.2 | 0.2 |
| Comparative Example 2 | Diarylamine Compound | Triarylamine Compound 2 | No | 0 | 0.3 | 0.3 |
| Comparative Example 3 | Diarylamine Compound | Triarylamine Compound 3 | No | 0 | 0.3 | 0.3 |
| Comparative Example 4 | Triarylamine Compound 1 | Triarylamine Compound 2 | No | 0.2 | 0.3 | 0.1 |
| Comparative Example 5 | Triarylamine Compound 1 | Triarylamine Compound 3 | No | 0.2 | 0.3 | 0.1 |
| Comparative Example 6 | Triarylamine Compound 2 | Triarylamine Compound 3 | No | 0.3 | 0.3 | 0 |
| Comparative Example 7 | Viologen Compound | Triarylamine Compound 1 | No | −0.9 | 0.1 | 1 |
| Comparative Example 8 | Viologen Compound | Triarylamine Compound 2 | No | −0.9 | 0.3 | 1.2 |
| Comparative Example 9 | Viologen Compound | Triarylamine Compound 3 | No | −0.9 | 0.3 | 1.2 |
| Comparative Example 10 | Viologen Compound | Diarylamine Compound | No | −0.9 | 0 | 0.9 |

TABLE 2

| | First Electrochromic Layer (First Electrochemical Reaction Layer) | | Second Electrochromic Layer (Second Electrochemical Reaction Layer) | |
|---|---|---|---|---|
| | Reversibly Oxidizable State (Yes: Present, No: Absent) | Reversibly Reducible State (Yes: Present, No: Absent) | Reversibly Oxidizable State (Yes: Present, No: Absent) | Reversibly Reducible State (Yes: Present, No: Absent) |
| Example 1 | Yes | Yes | Yes | No |
| Example 2 | Yes | Yes | Yes | No |
| Example 3 | Yes | Yes | Yes | No |
| Example 4 | Yes | Yes | Yes | No |
| Example 5 | Yes | Yes | Yes | No |
| Example 6 | Yes | Yes | Yes | No |
| Example 7 | Yes | Yes | Yes | No |
| Example 8 | Yes | No | No | Yes |
| Example 9 | Yes | No | No | Yes |
| Comparative Example 1 | Yes | No | Yes | No |
| Comparative Example 2 | Yes | No | Yes | No |
| Comparative Example 3 | Yes | No | Yes | No |
| Comparative Example 4 | Yes | No | Yes | No |
| Comparative Example 5 | Yes | No | Yes | No |
| Comparative Example 6 | Yes | No | Yes | No |
| Comparative Example 7 | No | Yes | Yes | No |
| Comparative Example 8 | No | Yes | Yes | No |
| Comparative Example 9 | No | Yes | Yes | No |
| Comparative Example 10 | No | Yes | Yes | No |

TABLE 3

|  | Test 1<br>Coloring Driving Test | Test 2<br>Decoloring Driving Test |
|---|---|---|
| Example 1 | A (30 minutes) | A (5 seconds) |
| Example 2 | A (20 minutes) | A (1 second) |
| Example 3 | A (20 minutes) | A (1 second) |
| Example 4 | A (30 minutes) | A (3 seconds) |
| Example 5 | A (30 minutes) | A (3 seconds) |
| Example 6 | A (30 minutes) | A (6 seconds) |
| Example 7 | B (8 minutes) | A (1 second) |
| Example 8 | B (8 minutes) | A (1 second) |
| Example 9 | B (8 minutes) | A (1 second) |
| Comparative Example 1 | C | — |
| Comparative Example 2 | C | — |
| Comparative Example 3 | C | — |
| Comparative Example 4 | C | — |
| Comparative Example 5 | C | — |
| Comparative Example 6 | C | — |
| Comparative Example 7 | B (3 minutes) | C |
| Comparative Example 8 | B (1 minute) | C |
| Comparative Example 9 | B (1 minute) | C |
| Comparative Example 10 | B (6 minutes) | C |

\* In Table 3, "—" in the column of the result of the decoloring driving test indicates "unmeasurable".

It is clear from the results of the driving test 1 that the elements of Examples 1 to 9 are capable of conducting a coloring driving and maintaining the color retention state for an extended period of time. The reason why the elements are capable of conducting a coloring driving is that one of the electrochemical reaction layers is oxidized before being bonded. As a result, when an oxidation reaction occurs in one of the electrochemical reaction layers, a reduction reaction occurs in the other one of the electrochemical reaction layers.

The color retention time is related to ΔE. Examples 1 to 6 showed good results because ΔE was as small as from 0.1 to 0.3 V. With regard to the decoloring driving in the driving test 2, the larger the ΔE, the better the result. As seen from the results of Examples 1 to 6, the decoloring driving could be completed within 10 seconds when ΔE was about 0.1 to 0.3 V.

In Example 7, although the result of the driving test 2 was good, the result of the driving test 1 indicates that color retention was slightly insufficient. This is considered to be related to the fact that ΔE is a large value of 0.5V.

In Comparative Examples 1 to 6, the requirement of "one of the first electrochemical reaction layer and the second electrochemical reaction layer is in a reversibly oxidizable state and the other is in a reversibly reducible state" is not satisfied, and coloring driving could not be performed in the driving test 1, confirming the necessity of oxidizing (putting in a radical cation state) one of the electrochemical reaction layers in advance.

In Comparative Examples 7 to 10, color retention and decoloring driving could not be performed sufficiently. The low values for color retention are considered to be due to the large ΔE.

In addition, it is considered that the decoloring driving was not completed because the viologen compound was used for one of the electrochemical reaction layers and had been naturally decolored by the influence of oxygen during color retention for 5 minutes.

From the above results, a device having excellent color retention property and drive stability even under the atmosphere is provided by controlling the oxidation-reduction potentials of the electrochemical reaction layers provided on both electrodes. An embodiment of the present invention provides a quite effective technique to produce an electrochromic element exhibiting excellent color retention property and drive stability even under the atmosphere without requiring strict sealing is provided.

Numerous additional modifications and variations are possible in light of the above teachings. It is therefore to be understood that, within the scope of the above teachings, the present disclosure may be practiced otherwise than as specifically described herein. With some embodiments having thus been described, it will be obvious that the same may be varied in many ways. Such variations are not to be regarded as a departure from the scope of the present disclosure and appended claims, and all such modifications are intended to be included within the scope of the present disclosure and appended claims.

The invention claimed is:

1. An electrochromic element comprising:
   a first substrate;
   a first electrode overlying the first substrate;
   a second substrate disposed at a distance from the first electrode;
   a second electrode overlying the second substrate;
   a first electrochemical reaction layer in contact with the first electrode;
   a second electrochemical reaction layer in contact with the second electrode; and
   an electrolyte layer between the first electrode and the second electrode,
   wherein one of the first electrochemical reaction layer and the second electrochemical reaction layer is in a reversibly oxidized state and the other is in a reversibly reduced state,
   wherein at least one of the first electrochemical reaction layer and the second electrochemical reaction layer is an electrochromic layer, and
   wherein the following formulae are satisfied:

$E1 \geq -0.8$ V (vs. FC/FC$^+$)

$E2 \geq -0.8$ V (vs. FC/FC$^+$)

where E1 represents an oxidation-reduction potential of the first electrochemical reaction layer and E2 represents an oxidation-reduction potential of the second electrochemical reaction layer.

2. The electrochromic element according to claim 1, wherein the following formula is further satisfied: $|E1-E2|<0.9$ V.

3. The electrochromic element according to claim 1, wherein the first electrochemical reaction layer and the second electrochemical reaction layer each comprise an electrochemically active material capable of being in a radical cation state,
   wherein at least one of the first electrochemical reaction layer and the second electrochemical reaction layer is constantly in the radical cation state, and
   wherein the following formulae are satisfied:

$E1' \geq -0.8$ V (vs. FC/FC$^+$)

$E2' \geq -0.8$ V (vs. FC/FC$^+$)

where E1' represents an oxidation-reduction potential between a neutral state and the radical cation state of the first electrochemical reaction layer and E2' represents an oxidation-reduction potential between a neutral state and the radical cation state of the second electrochemical reaction layer.

4. The electrochromic element according to claim 1, wherein the electrochromic layer develops color when in a radical cation state.

5. The electrochromic element according to claim 1, wherein only one of the first electrochemical reaction layer and the second electrochemical reaction layer is the electrochromic layer.

6. The electrochromic element according to claim 1, wherein the electrochromic layer contains a compound having a triarylamine backbone represented by the following general formula 1:

$$A_n\text{-}B_m \qquad \text{[General Formula 1]}$$

where m represents 0 when n is 2, or m represents 0 or 1 when n is 1; A has a structure represented by the following general formula 2 and bound to B at any of positions $R_1$ to $R_{15}$; and B has a structure represented by the following general formula 3 and bound to A at any of positions $R_{16}$ to $R_{21}$;

[General Formula 2]

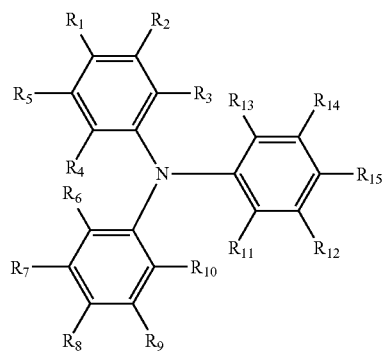

-continued

[General Formula 3]

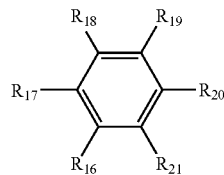

where $R_1$ to $R_{21}$ each independently represent monovalent organic groups and at least one of the monovalent organic groups is a radical polymerizable functional group.

7. The electrochromic element according to claim 1, wherein both the first electrochemical reaction layer and the second electrochemical reaction layer are electrochromic layers, and each of the electrochromic layers develops color when in a radical cation state.

8. A method for manufacturing an electrochromic element, comprising:
    forming a first electrode and a first electrochemical reaction layer on a first substrate;
    forming a second electrode and a second electrochemical reaction layer on a second substrate;
    bonding the first substrate and the second substrate via an electrolyte layer; and
    oxidizing at least one of the first electrochemical reaction layer and the second electrochemical reaction layer,
    wherein at least one of the first electrochemical reaction layer and the second electrochemical reaction layer is an electrochromic layer, and
    wherein the following formulae are satisfied:

$$E1 \geq -0.8 \text{ V (vs. FC/FC}^+\text{)}$$

$$E2 \geq -0.8 \text{ V (vs. FC/FC}^+\text{)}$$

where E1 represents an oxidation-reduction potential of the first electrochemical reaction layer and E2 represents an oxidation-reduction potential of the second electrochemical reaction layer.

* * * * *